| (12) | United States Patent | (10) Patent No.: | US 8,949,033 B2 |
|---|---|---|---|
| | Harakawa et al. | (45) Date of Patent: | Feb. 3, 2015 |

(54) METHOD FOR QUANTIFICATION OF NEUROTOXIN

(75) Inventors: Tetsuhiro Harakawa, Kumamoto (JP); Hirotoshi Nakano, Kumamoto-ken (JP); Yasushi Torii, Kumamoto (JP); Sachio Okuda, Kumamoto (JP); Ryuji Kaji, Tokushima (JP); Takashi Sakamoto, Ichikawa (JP); Motohide Takahashi, Musashimurayama (JP); Setsuji Ishida, Narashino (JP)

(73) Assignees: The Chemo-Sero-Therapeutic Research Institute, Kumamoto (JP); Japan as represented by Director General of National Institute of Infectious Diseases, Tokyo-To (JP)

( * ) Notice: Subject to any disclaimer, the term of this patent is extended or adjusted under 35 U.S.C. 154(b) by 1582 days.

(21) Appl. No.: 12/298,908

(22) PCT Filed: Apr. 28, 2006

(86) PCT No.: PCT/JP2006/309046
§ 371 (c)(1),
(2), (4) Date: Jul. 1, 2009

(87) PCT Pub. No.: WO2007/125604
PCT Pub. Date: Nov. 8, 2007

(65) Prior Publication Data
US 2009/0297452 A1      Dec. 3, 2009

(51) Int. Cl.
*G01N 33/50*      (2006.01)
*G01N 33/94*      (2006.01)

(52) U.S. Cl.
CPC ............ *G01N 33/5088* (2013.01); *G01N 33/94* (2013.01)
USPC ......................................................... 702/19

(58) Field of Classification Search
None
See application file for complete search history.

(56) References Cited

U.S. PATENT DOCUMENTS

| 5,358,945 | A | 10/1994 | Mizuchi et al. | |
| 7,452,335 | B2 * | 11/2008 | Wells et al. | ................ 600/554 |
| 2003/0032891 | A1 | 2/2003 | Jenkins | |
| 2004/0034645 | A1 | 2/2004 | Manabe et al. | |
| 2004/0260358 | A1 | 12/2004 | Vaughan et al. | |
| 2005/0163809 | A1 * | 7/2005 | Kaji et al. | ............... 424/239.1 |

FOREIGN PATENT DOCUMENTS

| EP | 1491205 | * 12/2004 |
| EP | 1491205 A | 12/2004 |
| JP | 2004223092 A | 8/2004 |
| JP | 2005509145 | 4/2005 |
| WO | 03015829 A2 | 2/2003 |
| WO | 2005062955 A2 | 7/2005 |

OTHER PUBLICATIONS

Herdegen et al., Brain Damage and Repair From Molecular Research to Clinical Therapy, copyright 2004, pp. 1-699.*
Cichon et al. (The Effect of Botulinum Toxin Type A Injection on Compound Muscle Action Potential in an In Vivo Rat Model, Laryngoscop, Feb. 1995, vol. 105, pp. 144-148).*
Kopman et al. (An Alternate Method for Estimating the Dose-Response Relationships of Neuromscular Blocking Drugs, Anesthesia Analg., 2000, No. 90, pp. 1191-1197).*
Kalden et al. (Studies on Experimental Automimmune Thymitis in Guinea-Pigs, Clin. Exp. Immunol., 1969, No. 5, pp. 319-340).*
Dodd et al.,"A Comparison of the Spread of Three Formulations of Botulinum Neurotoxin A as Determined by Effects on Muscle Function," European Journal of Neurology, 1998, pp. 181-186, vol. 5 No. 2.
Kopman et al., "An Alternate Method for Estimating the Dose-Response Relationships of Neuromuscular Blocking Drugs," Biosciences Information Service, 2000, Philadelphia, PA.
Hyeon et al.,"Effect of muscle activity and botulinum toxin dilution volume on muscle paralysis," Developmental medicine and child neurology, 2003, pp. 200-206, vol. 45, No. 3.
Jankovic, Botulinum toxin in movement disorders, Current Opinion in Neurology, 7:358-366 (1994).

(Continued)

*Primary Examiner* — Jason Sims
(74) *Attorney, Agent, or Firm* — Browdy and Neimark, PLLC

(57) ABSTRACT

The present invention relates to a method for quantitatively measuring the muscular relaxing activity of a neurotoxin. Specifically, based on an extent of the activity of muscular relaxation of a neurotoxin from bacteria of *Clostridium*, the present invention relates to a method for quantification of the efficacy (potential and/or diffusion reaction) of a neurotoxin comprising the following steps of: (a) administering a neurotoxin to the hind leg muscle of one of hind legs of a non-human mammal; (b) applying electric stimulus to said non-human mammal; (c) measuring a compound muscle action potential (CMAP) by contraction of said hind leg muscle to which the neurotoxin is administered and/or of the hind leg muscle of the other hind leg to which the neurotoxin is not administered; and (d) taking amplitude data from the compound muscle action potential (CMAP) obtained by the measurement in step (c) and analyzing an extent of a decrease in amplitude to thereby quantify the efficacy of the muscular relaxing activity by the neurotoxin. In contrast to the mouse $LD_{50}$ currently used as a potential unit of a botulinum toxin which is measurable at a level of only several units, the quantification method of the efficacy of a neurotoxin of the present invention allows for measurement at a level of as low as 0.01 to 1 unit and hence is a method with a high sensitivity, reproducibility and accuracy.

13 Claims, 5 Drawing Sheets

(56) References Cited

OTHER PUBLICATIONS

Kaji et al., Botulinum toxin—Wonder drug of this century, Dystonia and Botulinum therapy, Shindan-To-Chriyosha, (2005) (with English translation).

Schantz et al., Microbiological Methods Standardized Assay for *Clostridium botulinum* Toxins, Journal Assoc. Official Alalytic, 61:96-99 (1978).

Sesardic et al., Refinement and validation of an alternative bioassay for potency testing of therapeutic botulinum Type A toxin, Pharacol. Toxico, 78:283-288 (1996).

Pearce et al., Measurement of botulinum toxin activity: Evaluation of the lethality assay, Toxicol App. Pharma., 128:69-77 (1994).

Dressler et al., Electromyographic quantification of the paralysing effect of botulinum toxin in the sternocleidomastoid muscle, European Neurology, 43:13-16 (2000).

Cichon et al., The effect of botulinum toxin Type A injection on compound muscle action potential in an in vivo rat model, Laryngoscope, 105(2):144-148 (Feb. 1995).

Notice of Opposition issued in corresponding European Patent Application No. 06745899.0, mailed Aug. 20, 2012.

\* cited by examiner

METHOD FOR QUANTIFICATION OF NEUROTOXIN

TECHNICAL FIELD

The present invention relates to a method for quantitatively measuring the efficacy of a neurotoxin. Specifically, the present invention relates to a method for quantifying the effect of a neurotoxin with an index of a muscular relaxation in mammals. In some embodiment, the present invention provides a method for quantifying and defining "a potential" of a neurotoxin and/or "a diffusion reaction" from an administration site of a neurotoxin.

BACKGROUND ART

There is known a neurotoxin including one produced by bacteria of *Clostridium* or by several fish and shellfish, typically a swellfish poison tetrodotoxin, a snake toxin alpha-bungarotoxin, and the like. These toxins, though different in their point of action, commonly block neurotransmission at the nerve end to thereby exhibit a muscular relaxation in mammals to which the toxins are inoculated. Among these, *Clostridium* toxin is a neurotoxin produced by bacteria of *Clostridium* which is divided into more than a hundred groups based on the form and function. For bacteria of *Clostridium*, *Clostridium baratii*, *Clostridium butyricum*, *Clostridium botulinum*, *Clostridium tetani* and the like are known. A botulinum toxin produced by *Clostridium botulinum*, aerobic Gram-positive bacteria, is the most lethal neurotoxin on earth. It is classified into seven serotypes, A, B, C, D, E, F and G, and the property of each serotype has been elucidated. The serotypes are distinguishable from each other by respective serotype-specific neutralizing antibodies. Depending on the serotypes, a botulinum toxin may vary in animal species it may affect, severity of paralysis it induces, duration of time of its action, and the like.

An active center protein of a botulinum toxin has a molecular weight of about 150 kDa (NTX) as common in all the known seven serotypes. Any botulinum toxin, when produced from *Clostridium botulinum*, is a complex composed of NTX and a relevant nontoxic protein. A serotype A botulinum toxin is produced in a molecular form of either 900 kDa (LL toxin), 500 kDa (L toxin), or 300 kDa (M toxin) These LL, L and M toxins are called a botulinum toxin complex. These botulinum toxins are, upon absorption in the upper small intestine, degraded to release a nontoxic protein and an active center protein, NTX, under alkaline conditions (in a lymphatic vessel). The released NTX is then bound to a receptor at the nerve end at its C-terminus of a heavy chain and taken into neurons via the receptor. Then, it specifically cleaves a protein in the presynaptic membrane through a light chain zinc methaloendopeptidase activity and inhibits a calcium-dependant release of acetylcholine to thereby block neurotransmission at the synapse (Non-patent reference 1).

Although a botulinum toxin is a neurotoxin that may lead human to death in botulinum intoxication through blockage of systemic neurotransmission, it may also be utilized as a remedy for treating a disease with an accelerated muscular tension such as e.g. dystonia by positively making use of its activity and by administering directly into the muscle of a patient suffering from the disease so that a local muscular tension may be relieved (Non-patent reference 2). For instance, a serotype A botulinum toxin complex (BOTOX; registered trademark) has been approved as a medicament for treating blepharospasm, strabismus, hemifacial spasm, and cervical dystonia, and for treating wrinkles at the middle of the forehead by the Food and Drug Administration (FDA). A type B botulinum toxin complex (MYOBLOC; registered trademark) has also been approved as a medicament for treating cervical dystonia by FDA. It is said that a serotype A botulinum toxin has a higher potency and a longer duration of action as compared to serotypes other than a serotype A botulinum toxin. An average duration of action of a serotype A botulinum toxin from its single muscular administration up till amelioration of symptoms is typically about 3 to 4 months.

Currently, a biological potential of a therapeutic preparation of a botulinum toxin such as a serotype A botulinum toxin is indicated as a mouse $LD_{50}$ unit. One $LD_{50}$ is defined as $LD_{50}$ which is, based on intraperitoneal administration to mice, defined as an amount with which a half number of mice tested dies. Namely, a potential is quantified with a level or an amount of a neurotoxin with which mice die as a consequence of muscular relaxation. One $LD_{50}$, i.e. one unit, in mice of commercially available serotype A botulinum toxin complex (Allergan, Inc., BOTOX; registered trademark; containing 100 units in a glass vial) is about 50 pg.

However, it is reported that assays for determining a potential of a serotype A botulinum toxin with $LD_{50}$ unit in mice may vary widely from laboratory to laboratory (Non-patent reference 3). Some study planned for standardization of a serotype A botulinum toxin assay revealed that there was up to ten-fold difference in the results among 11 different laboratories (Non-patent reference 4). This variation however is not peculiar to an assay for a serotype A botulinum toxin. In fact, this assay has routinely been used as $LD_{50}$ in a toxicity test for a number of chemical drugs, solvents, cosmetics and medical drugs but many administrative organizations gave up requiring the routine use of this $LD_{50}$ for a toxicity test (Non-patent reference 5).

As such, as medical importance of the muscular relaxing activity of a botulinum toxin becomes highly recognized, an accurate quantification of the biological activity contained in a botulinum toxin preparation is needed in a manufacturing company and a laboratory as well as on clinical scene and up till the present a variety of quantification methods have been investigated.

Among the conventional methods for quantifying the botulinum toxin activity is a pinna reflex assay (Patent reference 1) where a botulinum toxin is administered to the levator auris longus muscle of rat and upon some duration of time quantification of the neurotoxin activity is performed with Electoromyograph using the auricle nerve. According to the teaching of this literature in which the auricle nerve is used and the cervical region of rat is excised for analysis, the same region needs be surgically excised for evaluating the effect of a botulinum toxin for a long period of time such as several days to several ten days. This however would be a burden to the animals used and thus it is not practical to use one and the same rat throughout the test but instead more rats will be necessary depending on days of the test. Furthermore, since a muscular region used for the test is small, said region is thought to be unsuitable for quantitatively evaluating a diffusion reaction in the muscle.

On the other hand, a method for determining the effect of a toxin (Patent reference 2), as reported, determines a potential of a botulinum toxin based on a muscular atrophy caused by administration of said toxin into the muscle of mammals. According to this method, however, a rat as administered with a botulinum toxin is sacrificed and the muscle at the site of administration is removed for analysis. Thus, for evaluating the effect of a botulinum toxin for a long period of time such as several days to several ten days, rats need be provided for respective days of measurement and hence many rats are necessary. Besides, as different rats are tested at each of days or under different conditions, a variation among the animals is thought to be high.

An electromyograph was also utilized for evaluating the effect of a botulinum toxin administered into the sternocleidomastoid muscle for therapeutic treatment of human suffering from cervical dystonia (Non-patent reference 5). For a surface electromyograph, a surface electrode is placed at a distance, usually of 1 to 3 cm, from the site of administration. A surface electrode may be utilized for measuring the magnitude and the range of a compound muscle action potential (CMAP) during the maximal voluntary contraction of the muscle to which the toxin is administered. It is envisaged that when a muscular paralytic effect initiated, a compound muscle action potential (CMAP) is decreased whereas, as a muscular paralytic effect is gradually waned, CMAP is increased. In this way, an electromyogram is used for judging the effect of a neurotoxin such as a botulinum toxin on the muscle or a group of muscles in individuals but non-quantitatively. The reason is that, as well known in the field of electric physiology, the electromyographic activity may vary among patients and, even in the same patient, may vary with the site of the muscle and days when administered. For instance, when the same patient is recorded simultaneously, the obtained repetitive surface electromyogram may significantly vary (i.e. from about 7% to about 20%). Furthermore, the range of the maximal voluntary contraction, as measured with surface electromyogram, may vary among patients.

In addition, the effect of administration of a serotype A botulinum toxin on a compound muscle action potential (CMAP) has been investigated using in vivo rat model (Non-patent reference 7). In this rat model, the effect on rat of difference in a dose of a neurotoxin is studied but quantification of a neurotoxin is not done.

Patent reference 1: U.S. Patent Publication No. 2003/0032891A1
Patent reference 2: Japanese patent publication No. 2005-509145 (WO2003/015829)
Non-patent reference 1: Jankovic, J. et al., Curr. Opin. Neurol., 1994, 7: p. 358-366
Non-patent reference 2: Ryuji Kaji et al., "Dystonia and botulinum therapy", Shindan-To-Chiryosha, 2005
Non-patent reference 3: Schantz and Kautter, J. Ass. of Anal. Chem., 1978, 61: p. 96-99
Non-patent reference 4: Sesardic et al., Pharacol. Toxico. 1996, 78: p. 283-288
Non-patent reference 5: Pearce et al., Toxicol. App. Pharm., 1994, 128: p. 69-77
Non-patent reference 6: Dressler et al., Electromyographic quantification of the paralyzing effect of botulinum toxin in the sternocleidomastoid muscle, Eur. Neurol. 2000; 43: p. 13-16
Non-patent reference 7: Cichon, Jr., M D et al., Laryngoscope, 1995 Feb., 105(2): p. 144-148

DISCLOSURE OF THE INVENTION

Technical Problem to be Solved by the Invention

A problem to be solved by the present invention is to provide a method for quantification of the activity of a botulinum toxin with a high precision in place of the mouse $LD_{50}$ currently used in a method for quantification of a potential of a botulinum toxin preparation. Since the effect aimed by the commercially available botulinum toxin preparations is to relax the muscle subject to therapeutic treatment, a necessary dose of a botulinum toxin is not $LD_{50}$ but a dose allowing for the muscular relaxing activity without lethality, which needs be evaluated quantitatively. Also, viewing that the mouse $LD_{50}$ is problematic due to its variability as described above, it is most important that a quantification system has a high accuracy. Besides, the mouse $LD_{50}$, as requiring for many mice, is also problematic from ethical point of view and for prevention of cruelty to animals. As such, a novel method for quantification of a botulinum toxin preparation is desired in place of the mouse $LD_{50}$.

Means for Solving the Problems

The present inventors have found that the efficacy of a neurotoxin could accurately be quantified by administering a neurotoxin such as a botulinum toxin to the hind leg muscle of a non-human mammal, and monitoring a compound muscle action potential (CMAP) of the hind leg muscle by electric stimulus, especially, taking into particular consideration amplitude data, by analyzing an extent of a decrease in amplitude by a neurotoxin and thus completed the present invention.

Thus, the present invention provides a method for quantification of the efficacy of a neurotoxin comprising the following steps of:
(a) administering a neurotoxin to the hind leg muscle of one of hind legs of a non-human mammal;
(b) applying electric stimulus to said non-human mammal;
(c) measuring a compound muscle action potential (CMAP) by contraction of said hind leg muscle to which the neurotoxin is administered and/or of the hind leg muscle of the other hind leg to which the neurotoxin is not administered; and
(d) taking amplitude data from the compound muscle action potential (CMAP) obtained by the measurement in step (c) and analyzing an extent of a decrease in amplitude to thereby quantify the efficacy of the muscular relaxing activity by the neurotoxin.

In step (c) above, when a compound muscle action potential (CMAP) by contraction of the hind leg muscle to which the neurotoxin is administered is measured, the efficacy of said neurotoxin may be quantified as a potential of said neurotoxin. On the other hand, when a compound muscle action potential (CMAP) by contraction of the hind leg muscle of the other hind leg to which the neurotoxin is not administered is measured, the efficacy of said neurotoxin may be quantified as a diffusion reaction of said neurotoxin. Furthermore, in step (c) above, when a compound muscle action potential (CMAP) by contraction of both the hind leg muscle to which the neurotoxin is administered and the hind leg muscle of the other hind leg to which the neurotoxin is not administered is measured simultaneously, the efficacy of said neurotoxin may be quantified simultaneously as both a potential and a diffusion reaction of said neurotoxin.

Analysis of an extent of a decrease in amplitude in step (d) above may be performed with CMAP analytical software.

CMAP analytical software used for the quantification method of the present invention serves as the following means:
(1) a means for extracting a maximum amplitude from electromyogram data obtained from an electromyograph for clinical diagnosis;
(2) a means for compiling and storing CMAP data from many animals so as to facilitate statistical analysis;
(3) a means for statistically analyzing CMAP amplitude data, as most well reflecting difference in a neurotoxin level using many animals, to ensure propriety of the data; and (4) a means for conducting various data analysis, using the data as complied in (3) above, in combination with any one of the following means:

(i) a means for statistically evaluating the reaction of a neurotoxin of a different kind and in a different dose with lapse of time;

(ii) a means for quantifying the efficacy of a sample;

(iii) a means for conjecturing the reaction of a neurotoxin with lapse of time;

(iv) a means for managing the quality of the efficacy of a sample; or (v) a means for statistically comparing the reaction of a neurotoxin of a different kind and in a different dose with lapse of time. Statistical analysis as used herein includes, but not limited to, regression analysis, Logit transformation, and the like.

In accordance with the quantification method of a neurotoxin of the present invention, unlike the conventional methods, a non-human mammal needs not be surgically treated for measurement.

A neurotoxin to be quantified by the quantification method of a neurotoxin of the present invention may be any having the activity of a neurotoxin and typically includes a neurotoxin from bacteria such as *Clostridium*, e.g. *Clostridium botulinum*.

The quantification method of a neurotoxin of the present invention may also be used for quantitatively comparing difference in the efficacy of different neurotoxins by quantifying the efficacy of two or more different neurotoxins.

In another aspect, the present invention provides a program for analyzing an extent of a decrease in amplitude of a compound muscle action potential (CMAP) by a neurotoxin, for serving as the following means:

(1) a means for extracting a maximum amplitude from electromyogram data obtained from an electromyograph for clinical diagnosis;

(2) a means for compiling and storing CMAP data from many animals so as to facilitate statistical analysis;

(3) a means for statistically analyzing CMAP amplitude data, as most well reflecting difference in a neurotoxin level using many animals, to ensure propriety of the data; and (4) a means for conducting various data analysis, using the data as complied in (3) above, in combination with any one of the following means:

(i) a means for statistically evaluating the reaction of a neurotoxin of a different kind and in a different dose with lapse of time;

(ii) a means for quantifying the efficacy of a sample;

(iii) a means for conjecturing the reaction of a neurotoxin with lapse of time;

(iv) a means for managing the quality of the efficacy of a sample; or (v) a means for statistically comparing the reaction of a neurotoxin of a different kind and in a different dose with lapse of time. Statistical analysis as used herein includes, but not limited to, regression analysis, Logit transformation, and the like.

In still another aspect, the present invention provides a computer-readable storage medium having a program for analyzing an extent of a decrease in amplitude of a compound muscle action potential (CMAP) by a neurotoxin, for serving as the following means:

(1) a means for extracting a maximum amplitude from electromyogram data obtained from an electromyograph for clinical diagnosis;

(2) a means for compiling and storing CMAP data from many animals so as to facilitate statistical analysis;

(3) a means for statistically analyzing CMAP amplitude data, as most well reflecting difference in a neurotoxin level using many animals, to ensure propriety of the data; and (4) a means for conducting various data analysis, using the data as complied in (3) above, in combination with any one of the following means:

(i) a means for statistically evaluating the reaction of a neurotoxin of a different kind and in a different dose with lapse of time;

(ii) a means for quantifying the efficacy of a sample;

(iii) a means for conjecturing the reaction of a neurotoxin with lapse of time;

(iv) a means for managing the quality of the efficacy of a sample; or (v) a means for statistically comparing the reaction of a neurotoxin of a different kind and in a different dose with lapse of time. Statistical analysis as used herein includes, but not limited to, regression analysis, Logit transformation, and the like.

As described above, an electromyograph is not suitable for quantitative evaluation in human clinics but may provide accurate results when an experimental animal is subject to measurement due to comparatively low individual difference. Furthermore, in accordance with the quantification method of the present invention, no surgical treatment such as excision or sacrifice may be done to a non-human mammal (e.g. rat) to which a botulinum toxin is administered. Thus, in accordance with the quantification method of the present invention, a long-term evaluation is enabled by measuring with lapse of time one and the same non-human mammal consecutively bred and a highly accurate quantification system may be provided that is less affected by difference in the time point when measured or difference in individuals. Furthermore, the quantification method of the present invention requires a smaller number of non-human mammals and hence is advantageous from ethical point of view and for prevention of cruelty to animals.

The quantification method of the present invention is characterized by that:

(1) it may quantify the potency of a neurotoxin by measuring the muscular relaxing activity of the neurotoxin in a smaller number of non-human mammals without surgical treatment using electromyograph, and especially taking into particular consideration amplitude data, by analyzing an extent of a decrease in amplitude by the neurotoxin;

(2) it may also quantitatively evaluate a diffusion reaction simultaneously with, or separately from, the quantification of a potential of a neurotoxin;

(3) it can measure a small amount of a neurotoxin at high sensitivity, which was impossible with the conventional mouse $LD_{50}$, and may consecutively and quantitatively evaluate a continuous reaction of a neurotoxin;

(4) it may quantitatively compare the efficacy among a different kind of neurotoxins to be measured with the evaluation of (2) and (3) above; and (5) it allows for quantification or quantitative comparison of enormous data obtained from the evaluation of (1) to (4) above by using a unique analytical software, in which statistical measure is incorporated, for simultaneously measuring and analyzing a potential and a diffusion reaction of a neurotoxin in a simple and prompt manner.

More Efficacious Effects than Prior Art

In accordance with the present invention, no surgical treatment such as excision or sacrifice is done to a non-human mammal (e.g. rat) to which a botulinum toxin is administered, and a long-term evaluation is enabled by measuring with lapse of time one and the same non-human mammal consecutively bred and a highly accurate quantification system may be provided that is less affected by difference in the time point when measured or difference in individuals. Furthermore, the quantification method of the present invention requires a smaller number of non-human mammals and hence is advantageous from ethical point of view and for prevention of cruelty to animals. With the present invention, it becomes possible in a smaller number of non-human mammals to quantify the efficacy (a potential and a diffusion reaction) of a neurotoxin, to simultaneously measure a potential and a diffusion reaction of a neurotoxin, and to quantitatively compare the efficacy of a neurotoxin of different kinds such as a neurotoxin vs. a progenitor toxin or respective serotypes of a neurotoxin.

It is envisaged that the use of this assay system may allow for calculation of a safe dose of a neurotoxin so as to avoid its spreading (a diffusion reaction) to the muscle other than the affected site in clinics and in addition may allow for calculation of a dose of a neurotoxin necessary for patients suffering from myotonia.

BEST MODE FOR CARRYING OUT THE INVENTION

Figure 1:
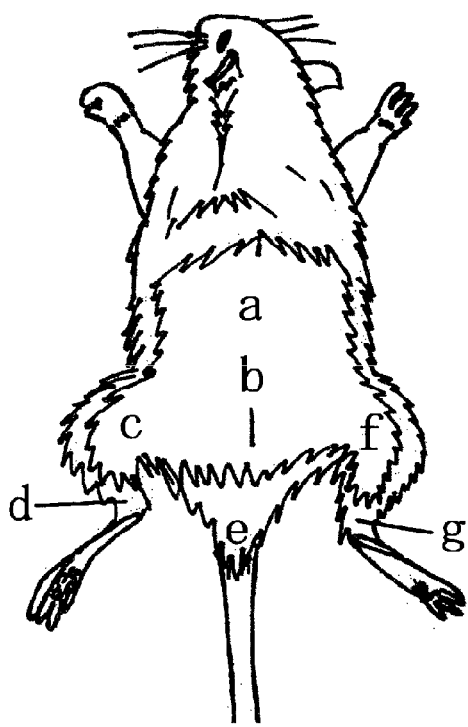
FIG. 1 shows an administration site and sites for measurement of a compound muscle action potential (CMAP) in a non-human mammal (rat) to which a neurotoxin is to be administered in the quantification method of the present invention.
(a): stimulating electrode (+);
(b): stimulating electrode (−);
(c): recording electrode (−) and administration site;
(d): recording electrode (+);
(e): ground electrode;
(f): electrode for recording diffusion (−);
(g): electrode for recording diffusion (+)

The term "efficacy" as used herein refers to an index of an amount of a certain chemical drug, e.g. a neurotoxin, necessary for inducing an extent of a physiological or chemical activity. For instance, an efficacy of a botulinum toxin means an extent or duration of term of inhibiting release of acetylcholine from a target tissue. Alternatively, an efficacy of a botulinum toxin means an extent of change in contraction of a certain muscle caused by a certain dose of a neurotoxin.

The term "potential" as used herein means a desirable efficacy of interest that is expressed numerically.

The term "diffusion reaction" as used herein means spreading of a neurotoxin to the muscle other than the affected site in clinics that is expressed numerically.

Quantification of the efficacy (a potential and/or a diffusion reaction) of a neurotoxin may be performed in accordance with the present invention by monitoring a compound muscle action potential (CMAP) of the hind leg muscle, preferably the quadriceps femoris, by electric stimulus using an electromyograph. In this regard, taking into particular consideration amplitude data among electromyogram parameters monitored with an electromyograph, a decrease in amplitude by a neurotoxin may be analyzed so as to accurately quantify the efficacy of a neurotoxin.

In a broad embodiment, the present invention encompasses a method for determining the efficacy of a neurotoxin which comprises administering a neurotoxin to the muscle of a non-human mammal and measuring the muscular relaxing activity in said muscle. Administration of a neurotoxin to the muscle of a non-human mammal and monitoring of a compound muscle action potential (CMAP) of the relaxed muscle allows for defining the effect of a neurotoxin as its efficacy. In one embodiment, the present invention provide for a method for determining the efficacy of a neurotoxin on the muscle. The term "non-human mammal" includes, for instance, monkey, rat, rabbit, guinea pig, hamster, cat, mouse and dog.

A neurotoxin to be quantified by the quantification method of a neurotoxin of the present invention may be any having the activity of a neurotoxin and may be selected from those derived from bacteria of *Clostridium* such as *Clostridium baratii*, *Clostridium butyricum*, *Clostridium tetani* and *Clostridium botulinum*. A botulinum toxin produced by *Clostridium botulinum* may be selected from serotypes A, B, C, D, E, F and G, and a mixture thereof, and typically serotype A botulinum toxin. These neurotoxins may be either a protein produced by natural bacteria or a recombinant protein or a chimeric protein prepared by a genetic recombination technique.

A botulinum toxin may be obtained by purification from a culture supernatant of *Clostridium botulinum* in accordance with the conventional technique (Sakaguchi, G., Ohishi, I. and Kozaki, S., 1981, BIOCHEMICAL ASPECTS of botulism: Purification and oral toxicities of *Clostridium* botulinum progenitor toxins, pp. 21-34, Lewis, G. E. (ed.), Academic Press, New York). Also, a variety of botulinum toxins are commercially available from e.g. Allergan Inc. (Irvin, Calif.), Ipsen Beaufour (France), Elan Pharmaceuticals (Ireland), List Biological Laboratories, Inc. (Campbell, Calif.); the Centre for Applied Microbiology and Research (Portondown, UK), Wako Pure Chemical Industries, Ltd. (Osaka, Japan), Metabiologics (Manson, Wis.), and Sigma Chemicals (St. Louse, Mo.).

An electromyograph may be one commercially available from Nicolet Biomedical (e.g. Nicolet Biking Quest series) as a medical instrument for therapy and diagnosis. An electromyograph is a medical instrument for test for conducting ElectroMyoGraphy: EMG. EMG is one of physiological tests for examining the presence of diseases from the nerve to the muscle. It has a stimulating electrode, a recording electrode (a different electrode), and an indifferent electrode (a reference electrode; so-called ground electrode), equipped with an electric stimulating device, a signal amplifying device such as an operational amplifier, a display and a recorder. An old-fashioned instrument is analogue one where a pen tolls from side to side on a moving roll paper. However, from the late 20th century onward, a majority of the instrument is one where signals obtained through an AD converter are processed not only for display but also for analysis. For its general use, an electrode is attached to the skin surface as near the muscle of interest as possible whereas two stimulating electrodes are attached as near the nerve controlling said muscle as possible. When electric stimulus is applied to the stimulating electrodes (pulse flow of electricity) and contraction of the muscle occurred, electromyogram is obtained. Electromyogram is read and a magnitude of the reaction, time delayed from the stimulus (conductive rate of motor neuron), the reaction to repetitive stimuli and the like are read out. These various test results are obtained.

The method of the present invention may accurately quantify the efficacy (a potential and/or a diffusion reaction) of a neurotoxin by using an electromyograph in a test mammal less affected by difference in individuals with no surgical treatment so as to quantitatively measure the efficacy. Also, the muscular relaxing activity in the muscle may vary depending on a dose of a neurotoxin. Thus, a dose-response curve may be constructed so as to determine the efficacy of a neurotoxin. As described above, it is envisaged that the efficacy as determined in accordance with the method of the present invention is more accurate and more reliable than the conventional $LD_{50}$.

The present invention will be explained herein for the case of rat but animal species to be used as well as sites where a neurotoxin is administered and sites for measurement are not limited thereto. First, a neurotoxin is administered to the left hind leg muscle. For measurement of a compound muscle action potential of the hind leg muscles, the vicinity of the lumber of rat is nipped with a clip electrode to apply electric excitement and a compound muscle action potential (CMAP) for each of the right and left hind leg muscles is recorded with recording electrodes. FIG. 1 shows sites where a neurotoxin is administered and sites where CMAP is measured. As the muscles are excited and the measurement is performed, amplitude of CMAP of the left hind leg muscle represents "a potential" whereas amplitude of CMAP of the right hind leg muscle represents "a diffusion reaction". Specifically, since a neurotoxin is injected to the left hind leg muscle in this case, amplitude of CMAP of the left hind leg muscle represents a muscular relaxing effect at the muscle to which the neurotoxin is administered. The higher the effect of a neurotoxin is, the smaller the obtained amplitude of CMAP becomes. On the other hand, amplitude of CMAP of the right hind leg muscle, as it is not the hind leg muscle where the neurotoxin is administered, indicates that the neurotoxin is dispersed to the muscle, other than one where the neurotoxin is administered, in which a muscular relaxing effect is exerted. In this case, the higher a diffusion reaction is, the smaller the obtained amplitude of CMAP becomes. For unit of amplitude of CMAP, numerical parameters such as an electric current or a potential may be used.

A neurotoxin is administered to the left hind leg muscle in rat at a variety of doses and CMAP data are obtained with an electromyograph to thereby provide for dose-dependant CMAP data for "a potential" and "a diffusion reaction". Also, after administration of a neurotoxin, CMAP may be measured with lapse of time to thereby provide for CMAP data showing the efficacy of a neurotoxin with lapse of time.

Linear regression of dose-dependant data for fixed days allows for quantification of "a potential" and "a diffusion reaction" of a neurotoxin as administered. In case of a neurotoxin of the same kind, it is also possible to calculate an unknown efficacy of the neurotoxin based on the formula obtained by analysis. Furthermore, after administration of a neurotoxin, CMAP is measured with lapse of time and the obtained CMAP data are shown in a graph for analysis to thereby calculate the number of days when the maximum reaction is exerted, the number of days required for recovery to the condition before administration, the number of days when 50% recovery rate is shown and the number of days when 50% reduction rate is shown. It is known that the efficacy and the duration of action may vary among the seven serotypes of a botulinum toxin. With the parameters described above, a quantitative comparison of the efficacy among the serotypes is possible.

Software is necessary for analysis. Although software for clinical diagnosis is attached to a commercially available electromyograph currently used as an instrument for clinical diagnosis, this is not sufficient for quantification of a neurotoxin. Accordingly, analytical software is necessary for statistically processing enormous data for automatically expressing numerically and averaging data of electromyogram parameters monitored with an electromyograph, in particular, amplitude data. By rendering this software to serve as statistical processing and as expressing in a graph and numerically, a simple and rapid analytical processing becomes possible.

CMAP analytical software used in the present invention may serve as a combination of processing of enormous data, statistical analysis, expressing in a numerical formula or a graph or illustration to thereby allow for quantification, expressing in a graph with lapse of time and comparison between different data.

CMAP analytical software used in the quantification method of the present invention may serve as the following means:

(1) a means for extracting a maximum amplitude from electromyogram data obtained from an electromyograph for clinical diagnosis;

(2) a means for compiling and storing CMAP data from many animals so as to facilitate statistical analysis;

(3) a means for statistically analyzing CMAP amplitude data, as most well reflecting difference in a neurotoxin level using many animals, to ensure propriety of the data; and (4) a means for conducting various data analysis, using the data as complied in (3) above, in combination with any one of the following means:

(i) a means for statistically evaluating the reaction of a neurotoxin of a different kind and in a different dose with lapse of time;

(ii) a means for quantifying the efficacy of a sample;

(iii) a means for conjecturing the reaction of a neurotoxin with lapse of time;

(iv) a means for managing the quality of the efficacy of a sample;

(v) a means for statistically comparing the reaction of a neurotoxin of a different kind and in a different dose with lapse of time.

(1) A Means for Extracting a Maximum Amplitude from Electromyogram Data Obtained from an Electromyograph for Clinical Diagnosis In analyzing electromyogram data obtained from an electromyograph for clinical diagnosis, maximum amplitude is extracted where electromyograph wave pattern is met with an equation of damped oscillation.

(2) A Means for Compiling and Storing CMAP Data from Many Animals so as to Facilitate Statistical Analysis As enormous CMAP data of different animals are obtained in a series of experiments, individual data are compiled and stored for statistical analysis.

(3) A Means for Statistically Analyzing CMAP Amplitude Data, as Most Well Reflecting Difference in a Neurotoxin Level Using Many Animals, to Ensure Propriety of the Data The individual data of (2) above are analyzed statistically for a maximum, a minimum, an average, a standard deviation and the like to thereby judge propriety of the data.

Furthermore, CMAP analytical software used in the present invention, in combination with any one of the following means, allows for analysis of various data, using the data compiled in (3) above.

(i) A Means for Statistically Evaluating the Reaction of a Neurotoxin of a Different Kind and in a Different Dose with Lapse of Time Difference in the efficacy of the same toxin with different doses or the reactivity of different toxins with the same dose with lapse of time is statistically compared and evaluated.

(ii) A Means for Quantifying the Efficacy of a Sample

Difference of the reactivity of the same toxin with different doses may be expressed numerically and quantified.

(iii) A Means for Conjecturing the Reaction of a Neurotoxin with Lapse of Time

It was found that the reaction of a neurotoxin with lapse of time is met with the formula:

$$y = a - b(\log(x)) + C(\log(x)\log(x))$$

which equation is one of those representing physical phenomenon. With this formula, there can be predicted the time when the neurotoxin reaction is reduced by 50%, the time when the neurotoxin reaction is recovered by 50%, the time when the neurotoxin reaction reached its maximum, the time when the neurotoxin reaction is recovered by 100%, and the like.

(iv) A Means for Managing the Quality of the Efficacy of a Sample

Data of stability of a preparation for a long period of time may be obtained, shown in figures and appropriately managed and evaluated.

(v) A Means for Statistically Comparing the Reaction of a Neurotoxin of a Different Kind and in a Different Dose with Lapse of Time The following empirical formula of the neurotoxin reaction with lapse of time may be calculated and the obtained formulas may be statistically compared.

$$y = a + b(\log(x)) + C(\log(x)\log(x))$$

A computer-readable storage medium having a program for analyzing an extent of a decrease in amplitude of a compound muscle action potential (CMAP) by a neurotoxin includes an ordinary storage medium such as floppy disk, CD-ROM, or DVD.

The present invention is explained in more detail by means of the following Examples but is not limited thereto.

Preparation 1

Purification of Botulinum Neurotoxin (1) Purification of Botulinum Serotype A, NTX Botulinum serotype A, M toxin, was purified as described by Sakaguchi, G., Ohishi, I., and Kozaki, S., 1981, BIOCHEMICAL ASPECTS of botulism: Purification and oral toxicities of *Clostridium* botulinum progenitor toxins, pp 21-34, Lewis, G. E.(ed.), Academic Press, New York.

The botulinum M toxin was dialyzed against 10 mM acetate buffer (pH 7.5), adsorbed to DEAE Sepharose column equilibrated with the same buffer, and eluted with 0 to 0.3 M NaCl gradient of the same buffer to separate the neurotoxin from a non-toxin protein. The obtained neurotoxin (NTX) was concentrated with YM-30 membrane (Millipore) to 1 mg/mL, dialyzed against 10 mM acetate buffer (pH 7.5) and stored at −80° C. till use.

(2) Purification of Three Serotypes of Botulinum Neurotoxin

Botulinum serotypes B, E and F neurotoxins were purified as described by Sakaguchi, G., Ohishi, I., and Kozaki, S., 1981, BIOCHEMICAL ASPECTS of botulism: Purification and oral toxicities of *Clostridium* botulinum progenitor toxins, pp 21-34, Lewis, G. E.(ed.), Academic Press, New York. The obtained neurotoxins were concentrated with YM-30 membrane (Millipore) to 1 mg/mL, dialyzed against 50 mM acetate buffer (pH 6.0) and stored at −80° C. till use.

Example 1

Figure 2:
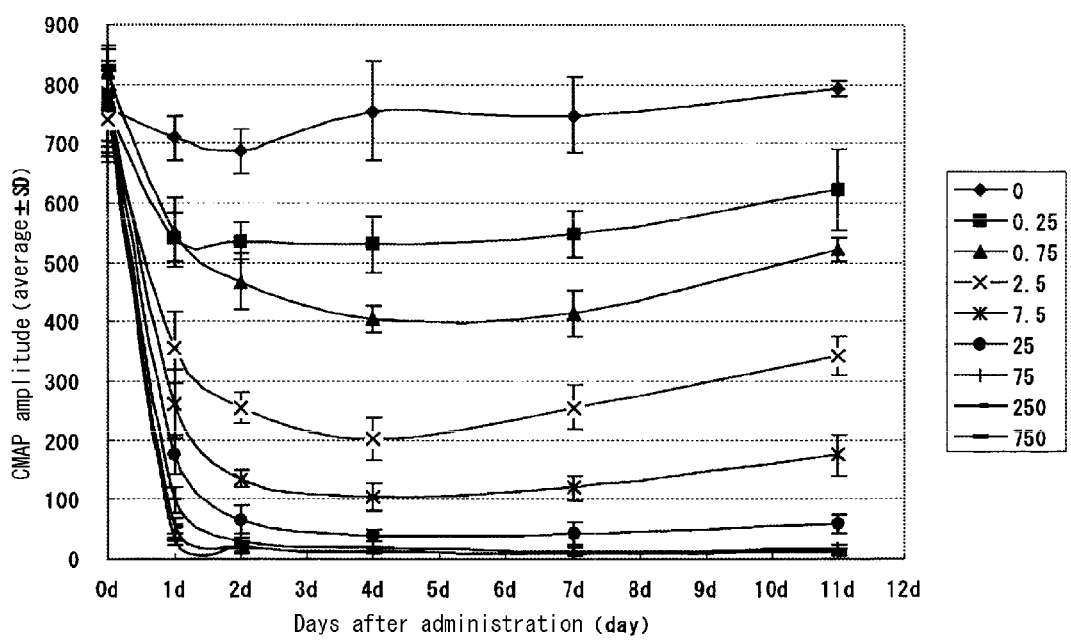
FIG. 2 is a graph that shows CMAP amplitude of the left hind leg muscle and days after administration when a neurotoxin at various concentrations is administered to the left hind leg muscle. The axis of abscissas depicts days after administration (day) whereas the axis of ordinates CMAP amplitude (mA).
Figure 3:
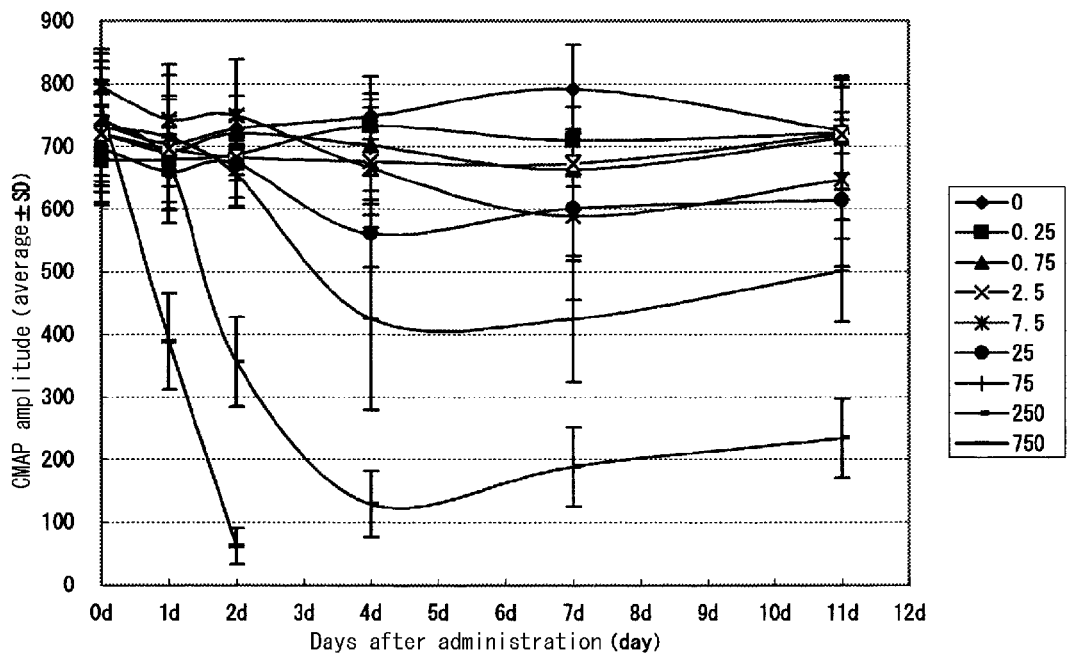
FIG. 3 is a graph that shows CMAP amplitude of the right hind leg muscle and days after administration when a neurotoxin at various concentrations is administered to the left hind leg muscle (i.e. measured at the site where the neurotoxin was not administered; quantification of a diffusion reaction). The axis of abscissas depicts days after administration (day) whereas the axis of ordinates CMAP amplitude (mA).

Dose-Dependant Inhibitory Effect to Neurotransmission of Botulinum Neurotoxin Serotype A and Quantitative Analysis Using Rat The serotype A, NTX, prepared in Preparation 1(1) was used (One unit of 1 $LD_{50}$ was about 25 pg when administered to mice intraperitoneally). A series of the neurotoxins were routinely prepared with sterile physiological saline containing 0.5 w/v % serum albumin to make 750, 250, 75, 25, 7.5, 2.5, 0.75, 0.25 and 0 (no toxin) pg/0.1 mL. Each 0.1 mL of the nine doses was administered to the left hind leg muscle of each SD rat and a compound muscle action potential (CMAP) of the hind legs was measured. For measurement of a compound muscle action potential of the hind leg muscles, the vicinity of the lumber of rat was nipped with a clip electrode to apply electric excitement and a compound muscle action potential (CMAP) for each of the right and left hind leg muscles (the quadriceps femoris) was recorded with recording electrodes. FIG. 1 shows sites where a neurotoxin was administered and sites where CMAP was measured. An electromyograph used was Nicolet Biking Quest series (Nicolet Biomedical). The results were numerically expressed and shown in a graph with "CMAP analytical software". FIGS. 2 and 3 show the results of a dose of the neurotoxin and amplitude of CMAP of the left and right hind legs, respectively.

Figure 4:
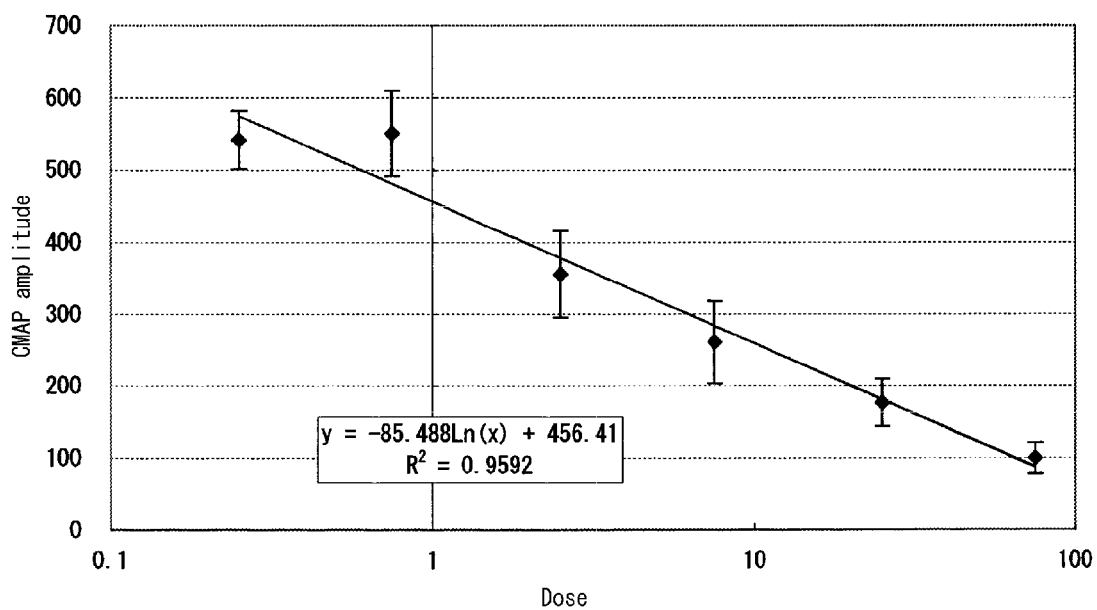
FIG. 4 is a calibration curve by linear regression of CMAP amplitude of the left hind leg muscle: quantification of a neurotoxin (on Day 1). The axis of abscissas depicts a dose (pg) whereas the axis of ordinates CMAP amplitude (mA).
Figure 5:
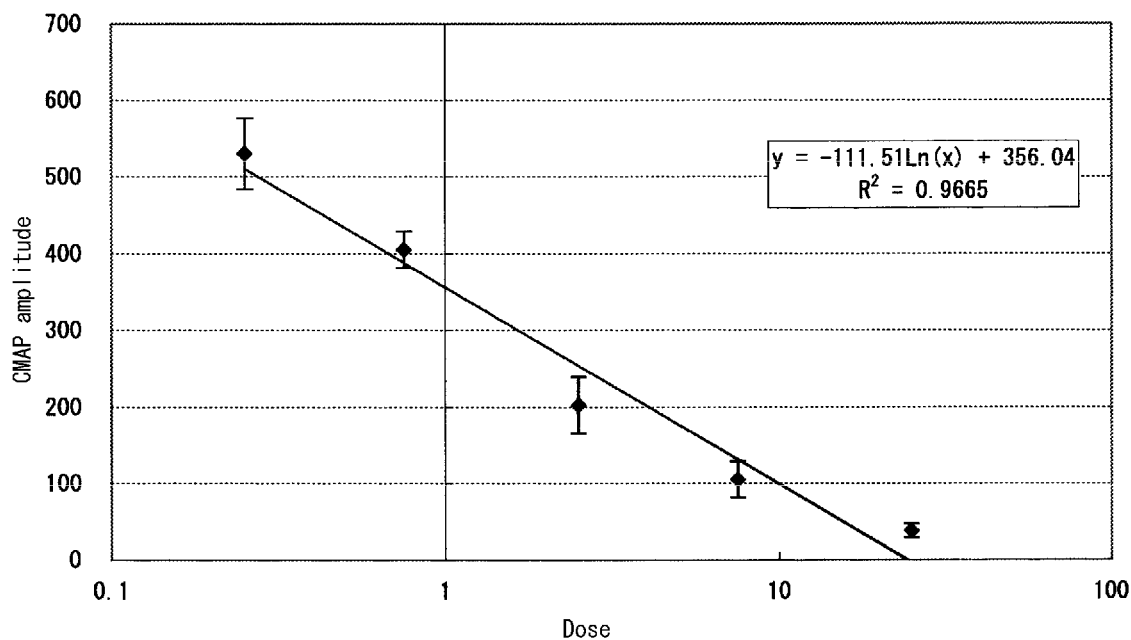
FIG. 5 is a calibration curve by linear regression of CMAP amplitude of the left hind leg muscle: quantification of a neurotoxin (on Day 4). The axis of abscissas depicts a dose (pg) whereas the axis of ordinates CMAP amplitude (mA).
Figure 6:
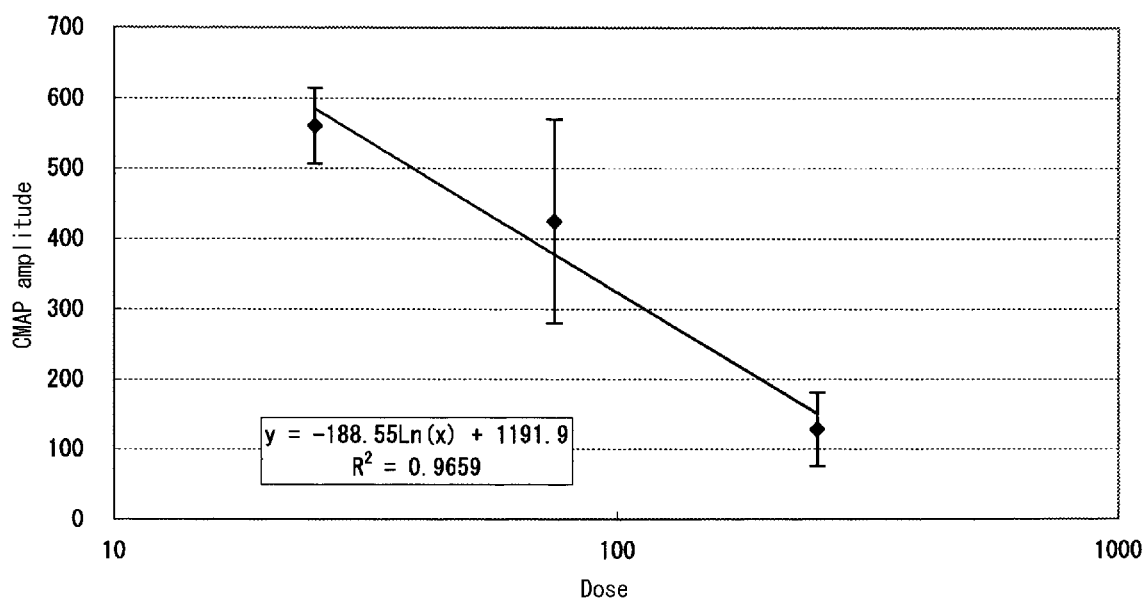
FIG. 6 is a calibration curve by linear regression of CMAP amplitude of the right hind leg muscle: quantification of a diffusion reaction (on Day 4). The axis of abscissas depicts a dose (pg) whereas the axis of ordinates CMAP amplitude (mA).

The data expressed numerically were subjected to regression analysis with "CMAP analytical software". FIGS. 4 and 5 show calibration curves obtained by linear regression of amplitude of CMAP of the left hind leg muscle and a dose of the neurotoxin, a day and four days after administration, respectively. Linear plotting was possible at any day after administration and was used as a calibration curve to determine a level of the neurotoxin in unknown samples from amplitude of CMAP. FIG. 6 shows a calibration curve obtained by linear regression of amplitude of CMAP of the right hind leg muscle and a dose of the neurotoxin, four days after administration. Linear plotting was also possible for amplitude of CMAP of the right hind leg muscle, the opposite of the muscle where the neurotoxin was administered, and was used as a calibration curve to determine a level of the neurotoxin in unknown samples from amplitude of CMAP for a diffusion reaction as well.

Figure 7:
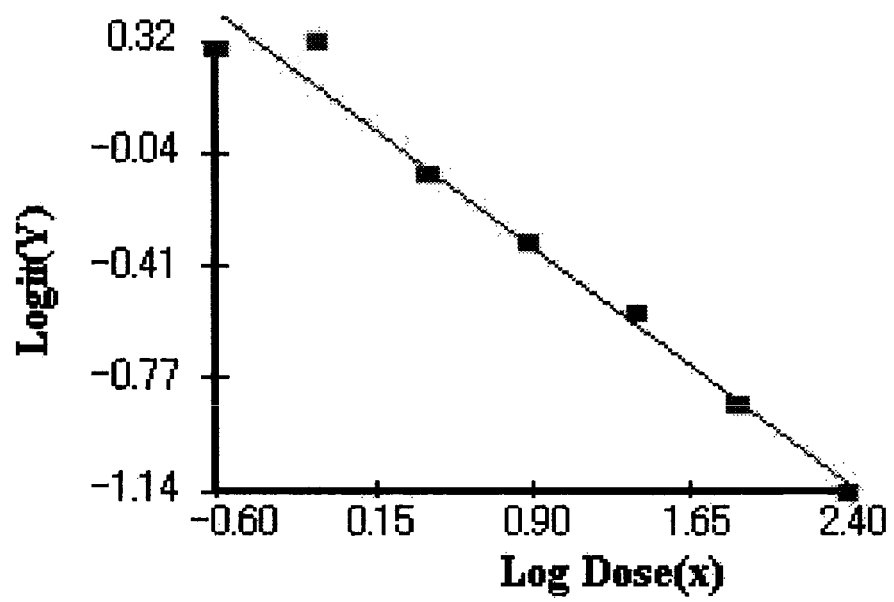
FIG. 7 is a calibration curve by Logit analysis of CMAP amplitude of the left hind leg muscle at a wide range of dose (on Day 1). X depicts a dose (pg) whereas Y CMAP amplitude (mA).
Figure 8:
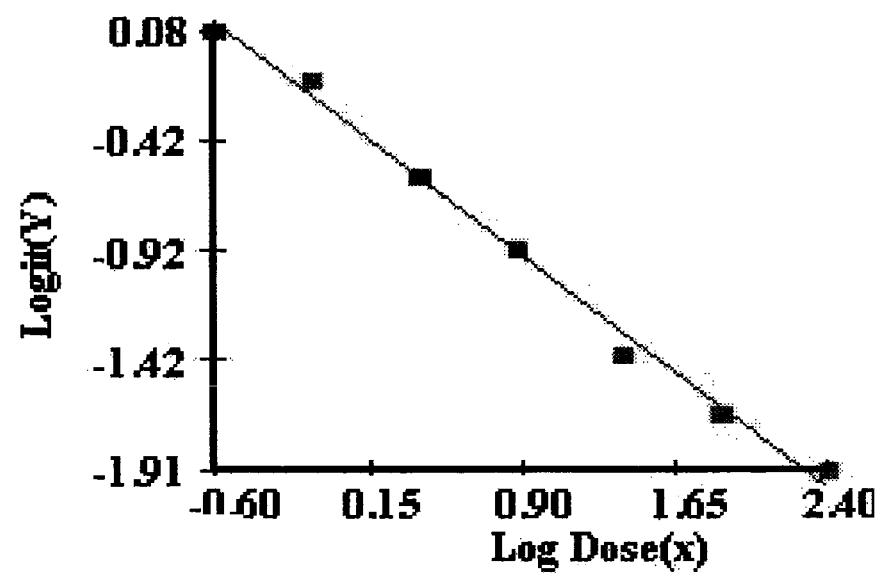
FIG. 8 is a calibration curve by Logit analysis of CMAP amplitude of the left hind leg muscle at wide range of dose (on Day 4). X depicts a dose (pg) whereas Y CMAP amplitude (mA).
Figure 9:
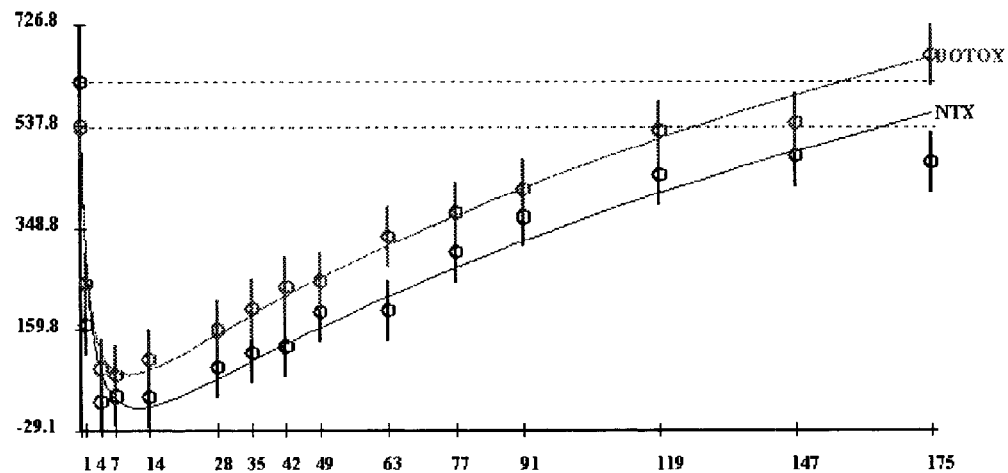
FIG. 9 shows a quantitative comparison of the efficacy between NTX and a botulinum toxin complex (BOTOX). The axis of abscissas depicts days after administration (day) whereas the axis of ordinates CMAP amplitude (mA).

In addition, the data expressed numerically were subjected to Logic conversion with "CMAP analytical software". FIGS. 7 and 8 show the results, a day and four days after administration, respectively. Logic analysis of amplitude of CMAP of the left hind leg muscle and a dose of the neurotoxin allowed for preparation of a calibration curve in a broader range of a dose of the neurotoxin than the regression analysis. This calibration curve was used to determine a level of the neurotoxin in unknown samples.

By using the method of the present invention, difference in the efficacy of a botulinum neurotoxin could be quantified at a level of several or lower units, which the conventional mouse $LD_{50}$ could not attain. Thus, the method of the present invention allows for detection of the efficacy of a neurotoxin at a 100-fold higher sensitivity than the mouse $LD_{50}$.

Example 2

Quantitative Comparison of Efficacy Between NTX and Neurotoxin Complex

The serotype A, NTX, prepared in Preparation 1(1) and BOTOX (registered trademark; Allergan, Inc.) were used. One unit was defined as 1 $LD_{50}$ when administered to mice intraperitoneally. Each of the neurotoxins was prepared with sterile physiological saline containing 0.5 w/v % serum albumin to make 1 mouse $LD_{50}/0.1$ mL. Each 0.1 mL of both neurotoxins was administered to the left hind leg muscle of each SD rat and a compound muscle action potential (CMAP) of the hind legs was measured. For measurement of a compound muscle action potential of the hind leg muscles, the vicinity of the lumber of rat was nipped with a clip electrode to apply electric excitement and a compound muscle action potential (CMAP) for the left hind leg muscle (the quadriceps femoris) was recorded with recording electrodes. FIG. 1 shows sites where a neurotoxin was administered and sites where CMAP was measured. An electromyograph used was Nicolet Biking Quest series (Nicolet Biomedical). The results were numerically expressed with "CMAP analytical software". The CMAP data of both neurotoxins of the left hind leg muscle were expressed in the formula: y=a−b Log(x)+c (Log(x)Log(x)) to thereby calculate the number of days when the maximum reaction was exerted, the number of days required for recovery to the condition before administration, the number of days when 50% recovery rate was shown and the number of days when 50% reduction rate was shown, so that the efficacy of both neurotoxins may quantitatively be compared (FIG. 2). As a result of quantitative comparison of the efficacy between both neurotoxins, as shown in Table 1, it was proved that NTX had higher durability and was more potent than the neurotoxin complex since NTX had longer days required for recovery to the condition before administration than the neurotoxin complex.

TABLE 1

|  | NTX | Botulinum toxin complex |
|---|---|---|
| No. of days when the maximum reaction was exerted | 11.6 | 9.7 |
| No. of days required for recovery to the condition before administration | 158.6 | 112.7 |
| No. of days when 50% recovery rate was shown | 73.0 | 47.4 |
| No. of days when 50% reduction rate was shown | 1.2 | 1.4 |

Example 3

Comparison of Efficacy of Four Serotypes of Botulinum Neurotoxin

Serotype A neurotoxin complex (BOTOX (registered trademark; Allergan, Inc.)) and three serotypes (B, E and F) of botulinum neurotoxin prepared in Preparation 1(1) were used. One unit was defined as 1 $LD_{50}$ when administered to mice intraperitoneally. A series of the neurotoxins were routinely prepared with sterile physiological saline containing 0.5 w/v % serum albumin to make 125, 25, 5, 1, 0.2, 0.1, 0.04 and 0 (no toxin) $LD_{50}/0.1$ mL. Each 0.1 mL of the eight doses was administered to the left hind leg muscle of each SD rat and a compound muscle action potential (CMAP) of the hind legs was measured. For measurement of a compound muscle action potential of the hind leg muscles, the vicinity of the lumber of rat was nipped with a clip electrode to apply electric excitement and a compound muscle action potential (CMAP) for the left hind leg muscle (the quadriceps femoris) was recorded with recording electrodes. FIG. 1 shows sites where a neurotoxin was administered and sites where CMAP was measured. An electromyograph used was Nicolet Biking Quest series (Nicolet Biomedical). The results were numerically expressed with "CMAP analytical software". Although an extent of neurotoxin unit measurable by the quantification system of the present invention varied depending upon serotypes, a dose-dependant reactivity could be confirmed.

Figure 10:
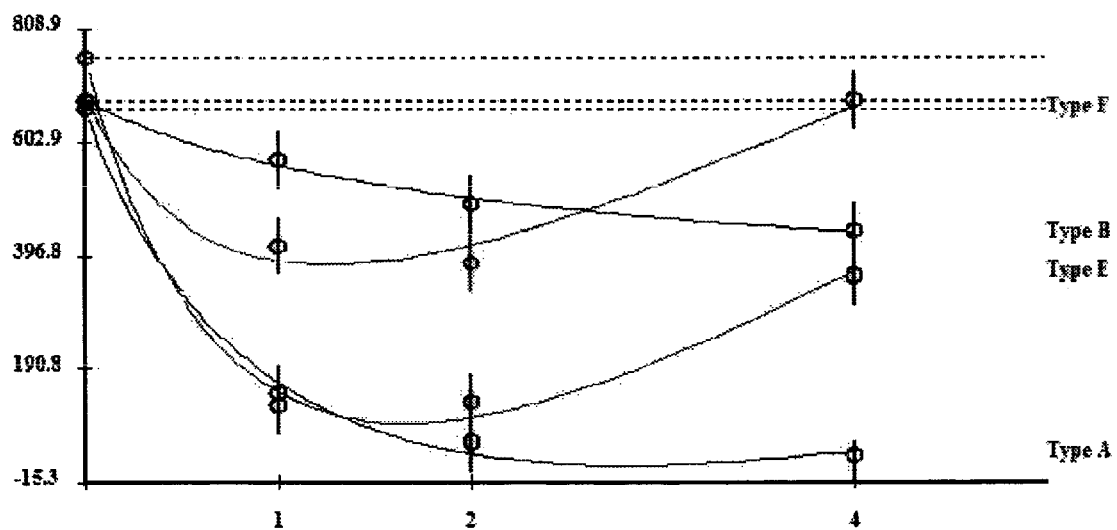
FIG. 10 shows a quantitative comparison of the efficacy among four serotypes of botulinum neurotoxin complexes. The axis of abscissas depicts days after administration (day) whereas the axis of ordinates CMAP amplitude (mA).

To show difference in the muscular relaxing activity among various serotypes of a botulinum neurotoxin, data obtained when administered at 1 $LD_{50}$ for serotype A, 5 $LD_{50}$ for serotypes E and F, or 125 $LD_{50}$ for serotype B, were expressed in a graph with "CMAP analytical software" (FIG. 10). Furthermore, the CMAP data of each neurotoxins of the left hind leg muscle were expressed in the formula: y=a−b Log(x)+c (Log(x)Log(x)) to thereby calculate the number of days when the maximum reaction was exerted, the number of days required for recovery to the condition before administration, the number of days when 50% recovery rate was shown and the number of days when 50% reduction rate was shown. As a result, as shown in Table 2, it was proved that serotype A had the highest durability and was the most potent, followed by serotypes E, F and B in this order. By using the method of the present invention, difference in the efficacy of a botulinum neurotoxin could be quantified at a level of several or lower units, which the conventional mouse $LD_{50}$ could not attain. Thus, the method of the present invention allows for detection of the efficacy of a neurotoxin at a 100-fold higher sensitivity than the mouse $LD_{50}$.

TABLE 2

| Serotype | A | B | E | F |
|---|---|---|---|---|
| No. of days when the maximum reaction was exerted | 2.8 | —※ | 1.7 | 1.3 |
| No. of days required for recovery to the condition before administration | 13.5 | | 6.1 | 4.1 |
| No. of days when 50% recovery rate was shown | 8.7 | | 4.0 | 3.1 |
| No. of days when 50% reduction rate was shown | 0.5 | | 0.4 | 0.4 |

※ Not calculated since the maximum reaction was exerted within 4 days

INDUSTRIAL APPLICABILITY

The quantification method of the present invention:
(1) may quantify the potency of a neurotoxin by measuring the muscular relaxing activity of the neurotoxin in a smaller number of non-human mammals without surgical treatment using electromyograph, and especially taking into particular consideration amplitude data, by analyzing an extent of a decrease in amplitude by the neurotoxin;
(2) also quantitatively evaluates a diffusion reaction simultaneously with, or separately from, the quantification of a potential of a neurotoxin;
(3) can measure a small amount of a neurotoxin at high sensitivity, which was impossible with the conventional mouse $LD_{50}$, and may continuously and quantitatively evaluate a consecutive reaction of a neurotoxin;
(4) may quantitatively compare the efficacy among a different kind of neurotoxins to be measured with the evaluation of (2) and (3) above; and
(5) allows for quantification or quantitative comparison of enormous data obtained from the evaluation of (1) to (4) above by using a unique analytical software, in which statistical measure is incorporated, for simultaneously measuring and analyzing a potential and a diffusion reaction of a neurotoxin in a simple and prompt manner.

Accordingly, it is envisaged that the use of this assay system may allow for calculation of a safe dose of a neurotoxin so as to avoid its spreading (a diffusion reaction) to the muscle other than the affected site in clinics and in addition may allow for calculation of a dose of a neurotoxin necessary for patients suffering from myotonia.

The invention claimed is:

1. A method for quantification of the efficacy of a neurotoxin, comprising the following steps of:
(a) administering a neurotoxin to the hind leg muscle of one of hind legs of a non-human mammal;
(b) applying electric stimulus to said non-human mammal with clip electrodes;
(c) measuring with clip electrodes a compound muscle action potential (CMAP) by contraction of said hind leg muscle to which the neurotoxin is administered and/or of the hind leg muscle of the other hind leg to which the neurotoxin is not administered; and
(d) taking amplitude data from the compound muscle action potential (CMAP) obtained by the measurement in step (c) and quantifying the efficacy of the muscular relaxing activity by the neurotoxin with calibration curves obtained by statistical analysis of the amplitude of CMAP.

2. The method for quantification of claim 1 wherein, in step (c), a compound muscle action potential (CMAP) by contraction of the hind leg muscle to which the neurotoxin is administered is measured.

3. The method for quantification of claim 1 wherein said efficacy is a potential of the neurotoxin.

4. The method for quantification of claim 1 wherein, in step (c), a compound muscle action potential (CMAP) by contraction of the hind leg muscle of the other hind leg to which the neurotoxin is not administered is measured.

5. The method for quantification of claim 1 wherein said efficacy is a diffusion reaction of the neurotoxin.

6. The method for quantification of claim 1 wherein, in step (c), a compound muscle action potential (CMAP) by contraction of both the hind leg muscle to which the neurotoxin is administered and the hind leg muscle of the other hind leg to which the neurotoxin is not administered is measured simultaneously to thereby simultaneously quantify both a potential and a diffusion reaction of the neurotoxin.

7. The method for quantification of claim 1 wherein an extent of a decrease in amplitude of a compound muscle action potential (CMAP) by the neurotoxin is analyzed in step (d) above.

8. The method for quantification of claim 1 wherein said statistical analysis is carried out by regression analysis or Logit transformation.

9. The method for quantification of claim 1 wherein a non-human mammal needs not be surgically treated for said measurement.

10. The method for quantification of claim 1 wherein the neurotoxin is selected from a neurotoxin from bacteria, of *Clostridium*, a neurotoxin produced by fish and shellfish, or a neurotoxin derived from a snake toxin.

11. The method for quantification of claim 10 wherein the neurotoxin is one from bacteria of *Clostridium* selected from *Clostridium baratii, Clostridium butyricum, Clostridium botulinum,* or *Clostridium tetani*.

12. The method for quantification of claim 11 wherein the neurotoxin is one from *Clostridium botulinum*.

13. The method for quantification of claim 1 wherein difference in the efficacy of two or more different neurotoxins is quantitatively compared.

* * * * *

UNITED STATES PATENT AND TRADEMARK OFFICE
CERTIFICATE OF CORRECTION

PATENT NO. : 8,949,033 B2
APPLICATION NO. : 12/298908
DATED : February 3, 2015
INVENTOR(S) : Tetsuhiro Harakawa et al.

It is certified that error appears in the above-identified patent and that said Letters Patent is hereby corrected as shown below:

On the title page item (86), delete "PCT/JP2006/309046" and insert --PCT/JP2006/309040--.

Signed and Sealed this
Ninth Day of June, 2015

Michelle K. Lee
*Director of the United States Patent and Trademark Office*